United States Patent
Ben-Noon

[11] Patent Number: 6,010,471
[45] Date of Patent: Jan. 4, 2000

[54] BODY TREATMENT APPARATUS

[75] Inventor: Asher Ben-Noon, Carmiel, Israel

[73] Assignee: Mego Afek Industrial Measuring Instruments, Kibbutz Afek, Israel

[21] Appl. No.: 08/835,582

[22] Filed: Apr. 9, 1997

[30] Foreign Application Priority Data

Apr. 15, 1996 [IL] Israel ............................. 117902

[51] Int. Cl.$^7$ .................................. A61H 15/00
[52] U.S. Cl. ................... 601/152; 601/151; 601/199
[58] Field of Search ................... 601/148, 149, 601/150, 151, 152; 602/13, 75

[56] References Cited

U.S. PATENT DOCUMENTS

| | | | |
|---|---|---|---|
| 3,513,842 | 5/1970 | Keenan et al. | 602/75 |
| 3,529,601 | 9/1970 | Kirkland | 602/75 |
| 3,862,629 | 1/1975 | Rotta . | |
| 4,013,069 | 3/1977 | Hasty . | |
| 4,030,488 | 6/1977 | Hasty . | |
| 4,374,518 | 2/1983 | Villanueva . | |
| 4,388,923 | 7/1982 | Gelfer et al. . | |
| 4,552,132 | 12/1985 | Ruscigno | 601/152 |
| 4,762,121 | 8/1988 | Shienfeld . | |
| 4,820,279 | 4/1989 | Dedo | 602/75 |
| 4,865,020 | 9/1989 | Bullard . | |
| 4,926,848 | 5/1990 | Shimkus et al. | 602/75 |
| 5,014,681 | 5/1991 | Neeman et al. . | |
| 5,372,575 | 12/1994 | Sebastian | 602/13 |

FOREIGN PATENT DOCUMENTS

| | | |
|---|---|---|
| 1175948 | 11/1958 | France . |
| 2246260 | 3/1977 | France . |
| 195 29 500 | 2/1997 | Germany . |

*Primary Examiner*—Danton D. DeMille
*Assistant Examiner*—Benjamin Koo
*Attorney, Agent, or Firm*—Browdy and Neimark

[57] ABSTRACT

Body treatment equipment for treatment of a body part, the body treatment equipment comprising an elongated band adapted to be spirally wound around the body part so as to encase the same with successive obliquely disposed turns and encompassing along its length a series of mutually juxtaposed, longitudinally disposed band segments adapted for respectively applying a compressive load to an underlying body part portion.

9 Claims, 4 Drawing Sheets

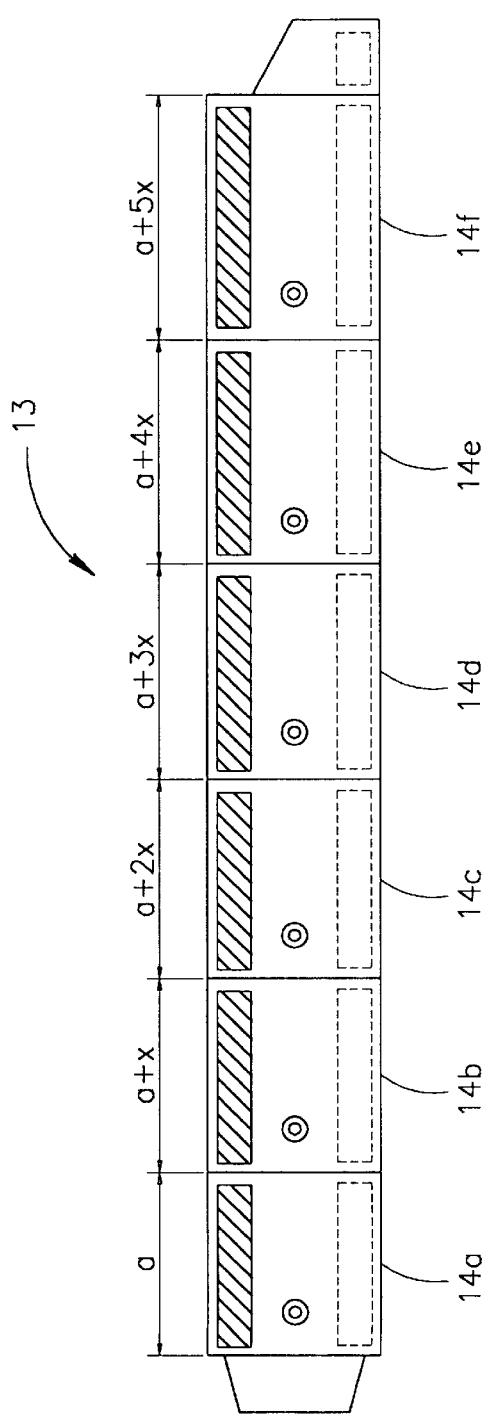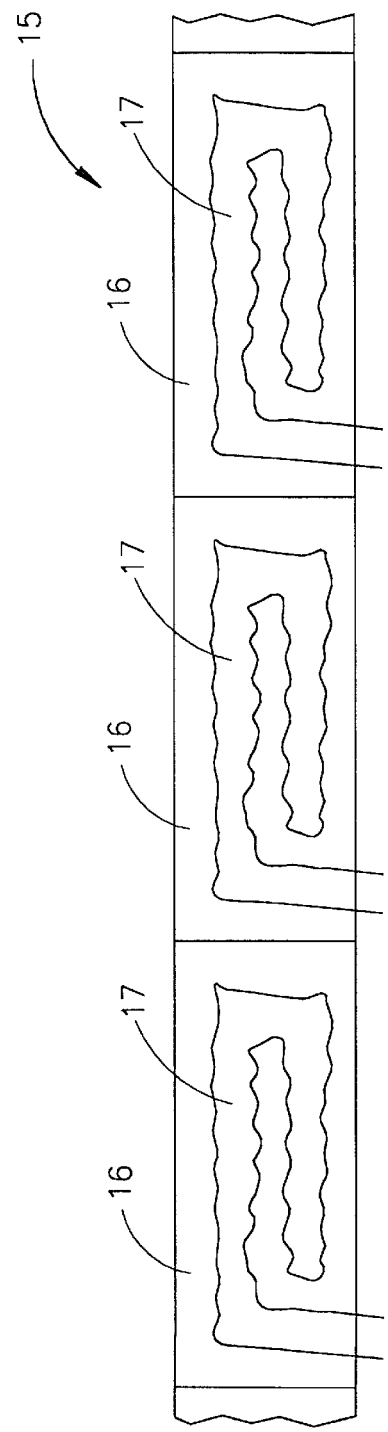
FIG. 6
FIG. 7

BODY TREATMENT APPARATUS

FIELD OF THE INVENTION

The present invention relates to body treatment equipment for the application of intermittent compression to a body part such as an upper or lower limb, for example, for the treatment of a number of medical disorders. The disorders include lymphatic disorders, venous disorders, and irregular muscular conditions either through strenuous activity or near complete inactivity.

BACKGROUND OF THE INVENTION

It is known to apply intermittent compression to an upper or lower limb by means of a sleeve, for example, as disclosed in U.S. Pat. Nos. 3,862,629, 4,013,069, 4,030,488 and 4,374,518, French Patent Nos. 1,175,948 and 73 35605 and U.S. Pat. Nos. 4,338,923, 4,762,121, 4,865,020 and 5,014,681 assigned to the same assignee as the present invention. In some of these known constructions, the sleeves are pre-formed for slipping onto a limb to be treated whilst in others, the sleeves are formed as flattened members for wrapping annularly around a limb to be treated and, thereafter, fastened therearound by suitable fastening means.

In DE 19529500 A1, there is described a woven composite with an extensive fabric weave in which is worked a thread or wire made from a memory possessing alloy connected to a controller for producing electrical pulses in the alloy thread so as to heat the same to either one of two operative alloy temperatures As and Ms both above the average temperature of a body part at which the alloy thread respectively contracts and returns to its original shape.

SUMMARY OF THE INVENTION

It is an object of the present invention to provide body treatment equipment for the application of intermittent compression to a body part, in particular, a body limb.

In accordance with the present invention, there is provided a body treatment equipment for treatment of a body part, the body treatment equipment comprising an elongated band adapted to be spirally wound around the body part so as to encase the same with successive obliquely disposed turns and encompassing along its length a series of mutually juxtaposed, longitudinally disposed band segments adapted for respectively applying a compressive load to an underlying body part portion.

The elongated band is preferably provided with releasably interlocking engaging means facilitating interengagement of successive obliquely disposed turns of the spirally wound band when applied to a body part to be treated. The interlocking engaging means is preferably of the fibrous-type whose pile-type component is deployed co-extensively along one longitudinal edge of the band's surface adapted to be outwardly disposed when the band is applied to a limb and whose hook-type component is deployed co-extensively along the band's opposing longitudinal edge of the band's surface adapted to be inwardly disposed when the band is applied to a limb, thereby facilitating the spirally wounding of the band from a limb's distal end to its proximal end.

Such an elongated band can be provided in different lengths and widths and formed with anywhere between 6 and 12 band segments depending on the size of the limb, be it a leg or an arm, to which it is intended to be applied. That notwithstanding, a suitably long elongated band can be equally applied to either an arm or a leg as opposed to the conventional sleeve constructions which were designed for only one type of body part.

In one implementation of the body treatment equipment, the elongated band is either prepared from two superimposed sheets of fluid impervious, resilient sheet material secured together along welding lines so as to integrally form inflatable cells respectively provided with fluid inlet and outlet means along its length or, alternatively, sheet material formed with pockets for removably receiving suitably shaped and sized individually formed inflatable cells respectively provided with fluid inlet and outlet means. In another implementation of the body treatment equipment, the band segments are provided with independently operable memory possessing alloy threads as described in DE 19529500 A1.

There is also provided in accordance with the present invention, a therapeutic method of treating a body part by applying intermittent compression thereto, the method comprising the steps of:

(a) encasing a body part with a series of obliquely disposed band segments extending in the proximate direction of the body part; and (b) cyclically applying compressive loads to underlying body part portions in a predetermined sequence.

It is believed that the provision of band segments spirally wound around a limb so as to encase the same with obliquely disposed turns will improve treatment in comparison to annularly disposed band segments as hitherto obtained with conventional sleeves. This belief is based on the fact that spirally wound band segments would tend to effect a more gradual and continuous milking action in the proximal or venous direction than annularly disposed band segments.

This more gradual and continuous milking action can be further facilitated by creating a positive pressure gradient in each band segment in the proximal direction. In the first embodiment, this is achieved by disposing each inflatable cell's fluid inlet and outlet means towards its distal end whilst, in the second embodiment, this is achieved by connecting the distal end of the memory possessing alloy thread to a controller for providing electrical current pulses. This more gradual and continuous milking action can be still further facilitated by the provision of band segments of gradually increasing length in the proximal direction.

BRIEF DESCRIPTION OF THE DRAWINGS

For a better understanding of the present invention and to show how the same can be carried out in practice, reference will now be made, by way of non-limiting examples only, to the accompanying drawings in which:

FIG. 6 is a top view of a third embodiment of body treatment equipment in accordance with the present invention; and FIG. 7 is a top view of a fourth embodiment of body treatment equipment in accordance with the present invention.

DETAILED DESCRIPTION OF THE DRAWINGS

Figure 1:
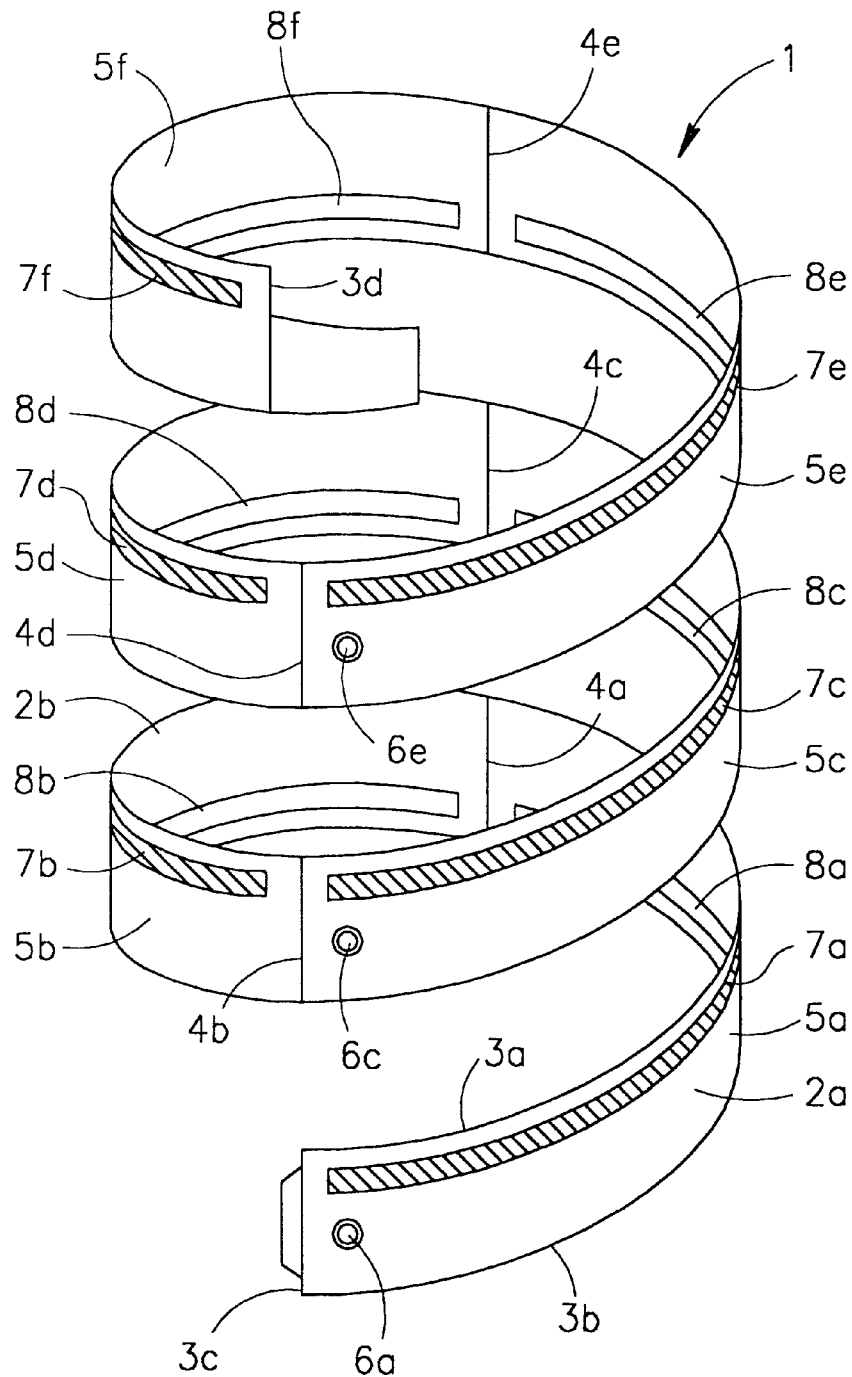
FIG. 1 is a perspective view of a preferred embodiment of body treatment equipment in accordance with the present invention.

FIG. 1 depicts an elongated band, generally designated 1, comprising two superimposed generally rectangular shaped sheets 2a and 2b preferably made from a fluid impervious, resilient sheet material, for example, nylon fabric coated with polyurethane. The sheets 2a and 2b are integrally secured together along opposing longitudinal edges 3a and 3b and opposing transverse edges 3c and 3d and at regularly spaced intervals along their lengths by transversely disposed bonding lines 4a–4e so as to form a series of mutually juxtaposed, longitudinally disposed inflatable cells 5a–5f (constituting band segments).

One of the sheets 2a and 2b, in this case the sheet 2a, is adapted to be outwardly disposed when applied on a limb and, as such, is provided with, for each of the inflatable cells 5a–5f, a series of ports 6a–6f for connecting via an appropriate selector unit (not shown) to a source of compressed air (not shown) for enabling the inletting and outletting of compressed air with respect thereto so as to individually inflate or deflate its respective cell. The ports 6a–6f are preferably disposed toward the distal end of their respective cells 5a–5f. In addition, the sheet 2a is provided with a series of pile-type fastening strips 7a–7f substantially co-extensive with the band's upper longitudinal edge, namely in this case longitudinal edge 3a.

The other sheet adapted to be inwardly disposed when applied to a limb, namely in this case the sheet 2b, is provided with, for each of the inflatable cells 5a–5f, a series of hook-type fastening strips 8a–8f substantially co-extensive with the band's lower longitudinal edge 3b. The respective pile-type and hook-type fastening strips 7 and 8 are preferably of the Velcro™ interlocking fibrous-type fastener.

Figure 2:
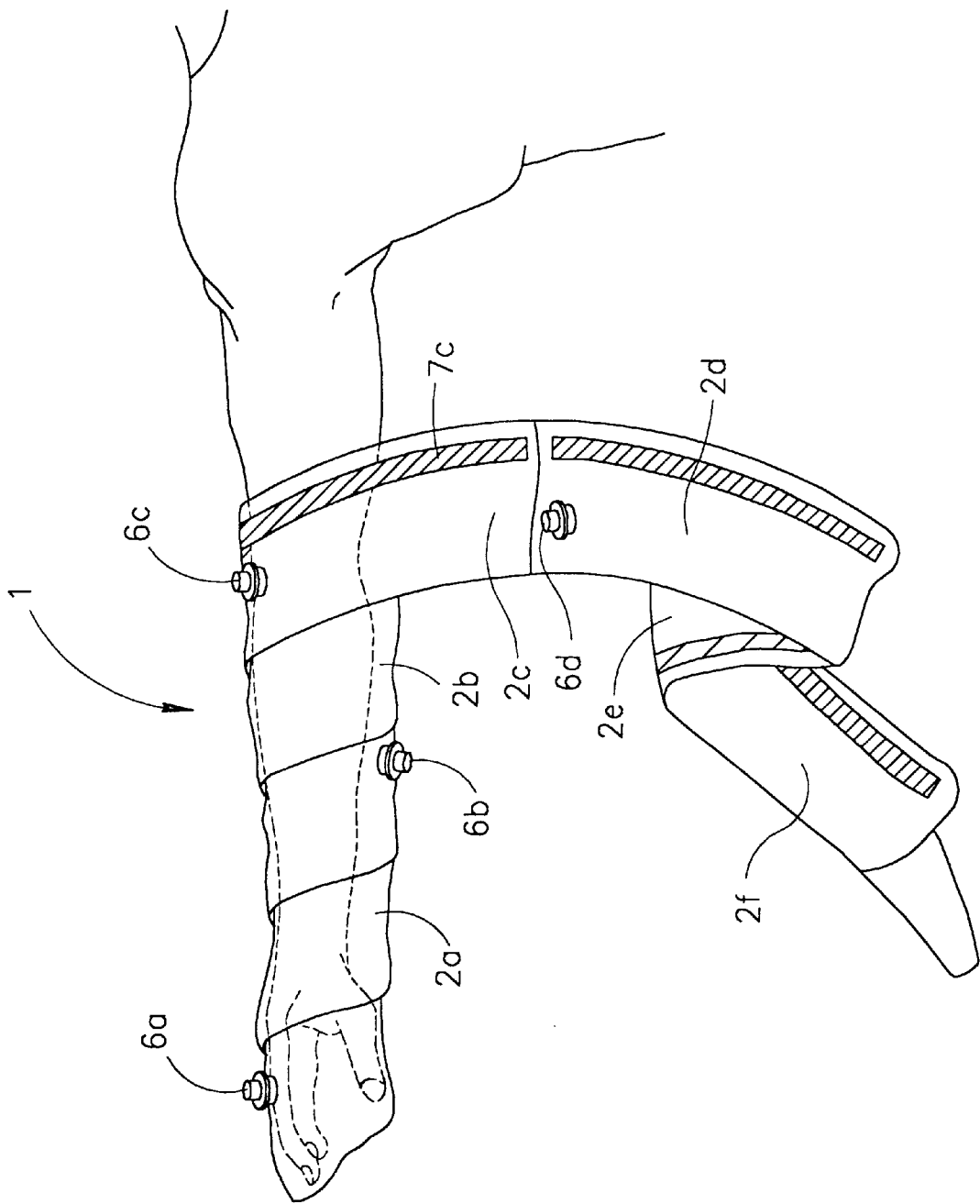
FIG. 2 is a view of the body treatment equipment of FIG. 1 being spirally wound along an arm in a proximal direction so as to encase the same.

FIG. 2 shows the application of the band 1 to a patient's limb, in this case, his right arm by the steps of first juxtaposing one end of the band 1 to the distal end of his arm and thereafter spirally winding the band 1 along his arm through the interengagement of hook-type fastening strips on pile-type fastening strips such that there are successively overlapping obliquely disposed turns extending from the distal end of the user's arm to its proximate end, thereby creating an effectively continuous sleeve along the user's arm. Depending on the number of inflatable cells in the band 1 and a particular location selected along the user's arm, the interengagement can be between leading and trailing portions of the same inflatable cells or between adjacent portions of different cells.

Once the band 1 has been securely applied to the patient's arm, depending on the particular medical disorder to be treated, treatment can applied in accordance with one of two common modes of operation. In one mode of operation, a single cycle involves successively inflating the cells in a proximal direction until such time that all the cells are simultaneously inflated at which time they are all deflated before the commencement of a second cycle. Whilst, in a second mode of operation, a travelling compression wave is induced in the band as taught in U.S. Pat. No. 5,014,681 assigned to the same assignee as the present invention and incorporated herein by reference. Briefly stated, the travelling compression wave is induced by the inflation of one group of cells whilst at least partially deflating the preceding group of cells and ensuring that all the cells are simultaneously deflated for a minimal time period between successive cycles of operation.

Figure 3:
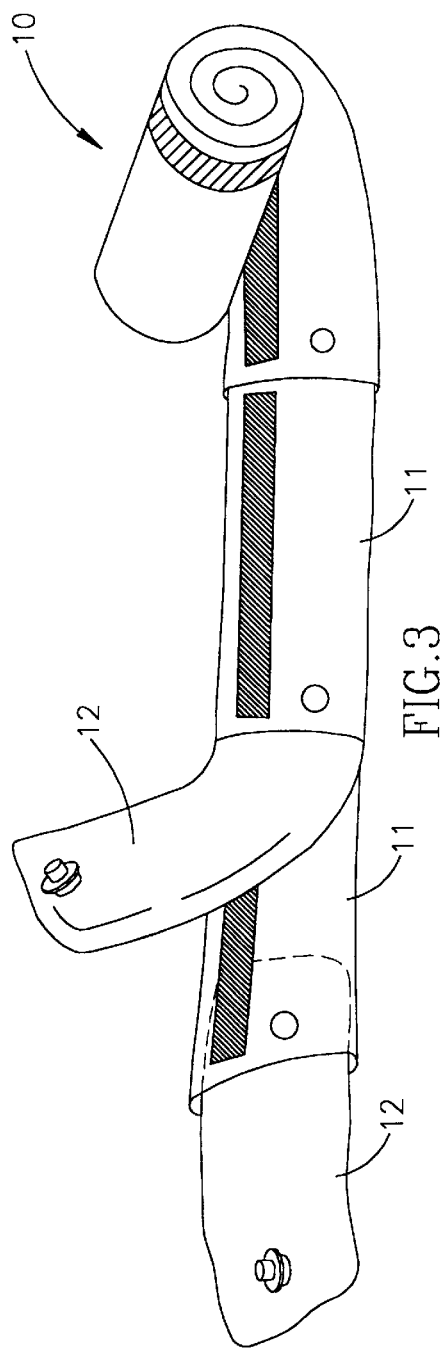
FIG. 3 is a schematic view a second embodiment of body treatment equipment in accordance with the present invention.
Figure 4:
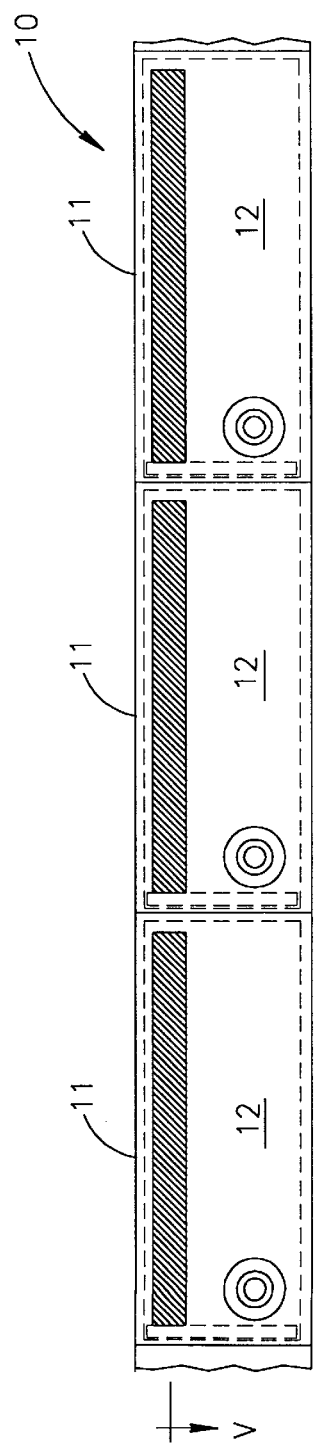
FIG. 4 is a top view of the body treatment equipment of FIG. 3.
Figure 5:
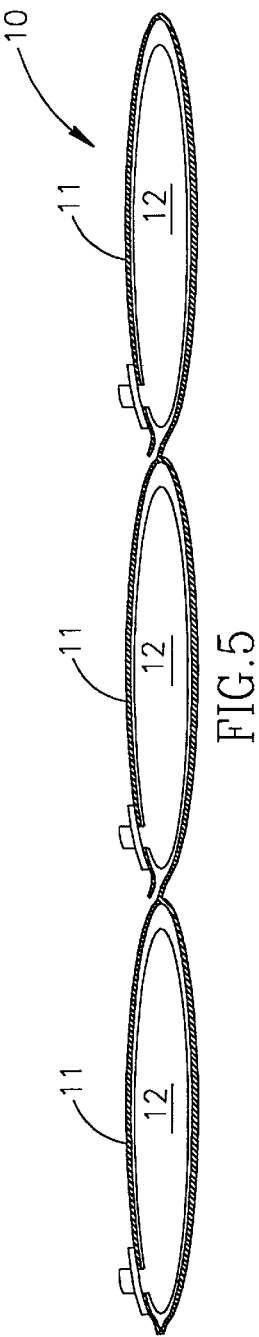
FIG. 5 is a cross section view of the body treatment equipment of FIG. 3 along line V—V in FIG. 4.

FIGS. 3–5 depict an elongated band, generally designated 10, having a similar construction to the elongated band 1, the main difference residing therebetween being that the former includes a series of pockets 11 each adapted for receiving therein a removable inflatable cell 12.

FIG. 6 depicts an elongated strip, generally designated 13, having a similar construction to the elongated band 1, the main difference residing therebetween being that the former includes a series of inflatable cells 14a–14f having progressively increasing lengths from the end of the band 13 adapted to be placed at the distal end of a body limb to the end of the band 13 adapted to be placed at the proximal end of a body limb.

FIG. 7 depicts an elongated band, generally designated 15, having a similar construction to the elongated band 1, the main difference residing therebetween being that the former includes a series of band segments 16 each provided with a memory possessing alloy thread 17 connected to a controller (not shown) for producing electrical current pulses.

While the invention has been described with respect to a limited number of embodiments, it will be appreciated that many variations, modifications and other applications of the invention can be made by those ordinarily skilled in the art.

I claim:

1. Body treatment equipment for treatment of a body limb, the body treatment equipment comprising an elongated band adapted to be spirally wound around the body part so as to encase the same with successive obliquely disposed turns and encompassing along its length a series of mutually juxtaposed, longitudinally disposed band segments adapted for respectively applying a compressive load to an underlying body part portion, wherein each of said band segments comprises an integrally formed inflatable cell provided with fluid inlet and outlet means.

2. Body treatment equipment according to claim 1 wherein said elongated band further comprises releasably interlocking engaging means facilitating interengagement of said successive obliquely disposed turns of said spirally wound band.

3. Body treatment equipment according to claim 2 wherein said releasably interlocking engaging means comprises a first-type fastening strip disposed on a first surface of said band so as to be substantially co-extensive with a first longitudinal edge of said band and a second-type fastening strip disposed on a second surface of said band so as to be substantially co-extensive with a second longitudinal edge of said band.

4. Body treatment equipment according to claim 3 wherein said engaging means is of the interlocking fibrous-type.

5. Body treatment equipment according to claim 1 wherein said band segments are of progressively increasing length.

6. Body treatment equipment according to claim 1 wherein each of said band segments comprises a pocket adapted for removably receiving an inflatable cell provided with fluid inlet and outlet means.

7. Body treatment equipment according to claim 1 wherein each of said integrally formed inflatable cells has its fluid inlet and outlet means disposed toward its distal end for applying a positive pressure gradient in a direction corresponding to the direction of venous blood flow in the body part.

8. Body treatment equipment for treatment of a body limb, the body treatment equipment comprising an elongated band having sufficient flexibility to be spirally wound around the body limb so as to spirally encase the limb with successive obliquely disposed turns, said elongated band comprising a series of longitudinally disposed band segments located end-to-end with respect to one another, each said band segment being controllable separately or independently of one another for applying a compressive load to an underlying part of said limb to sequentially and progressively apply a positive pressure gradient in a direction of venous blood flow in the body limb, each band segment comprising an integrally formed inflatable cell having a fluid inlet and a fluid outlet, means for controlling said application of a compressive load, and means for preventing the unraveling of said elongated band during application of the compressive load.

9. A therapeutic method of treating a body part by applying intermittent compression thereto, the method comprising the steps of:

(a) encasing a body part with a series of obliquely disposed band segments extending in a direction of venous blood flow of the body part by spirally winding an elongated band encompassing along a length thereof a series of mutually juxtaposed, longitudinally disposed band segments around the body part in said blood flow direction so as to encase the body part with a series of obliquely disposed turns which overlap so as to constitute an effectively continuous sleeve, said band segments each comprising an integrally formed inflatable cell provided with a fluid inlet and a fluid outlet; and (b) cyclically applying compressive loads to underlying body part portions in a predetermined sequence.

* * * * *